United States Patent [19]

Miike et al.

[11] Patent Number: 4,851,353

[45] Date of Patent: * Jul. 25, 1989

[54] METHOD AND TEST COMPOSITION FOR DETERMINATION OF LIPID PEROXIDE

[75] Inventors: Akira Miike; Yoshiaki Shimizu, both of Shizuoka; Toshio Tatano, Numazu; Katsuyuki Watanabe, Higashimucayama, all of Japan

[73] Assignee: Kyowa Hakko Kogyo Co., Ltd., Tokyo, Japan

[*] Notice: The portion of the term of this patent subsequent to May 17, 2000 has been disclaimed.

[21] Appl. No.: 11,401

[22] Filed: Feb. 4, 1987

Related U.S. Application Data

[63] Continuation of Ser. No. 858,088, Apr. 29, 1986, abandoned, which is a continuation of Ser. No. 758,566, Jul. 24, 1985, abandoned, which is a continuation of Ser. No. 522,006, Nov. 14, 1983, abandoned, which is a continuation of Ser. No. 445,431, Nov. 30, 1982, abandoned, which is a continuation of Ser. No. 253,546, Apr. 13, 1981, abandoned.

[30] Foreign Application Priority Data

Apr. 14, 1980 [JP] Japan ............................ 55-48939

[51] Int. Cl.$^4$ ...................... G01N 21/78; G01N 33/92
[52] U.S. Cl. ........................................ 436/71; 422/56; 435/28; 436/66; 436/124; 436/125; 436/135; 436/164; 436/904
[58] Field of Search ................. 436/66, 135, 904, 164, 436/124, 125, 71; 422/56; 435/28; 544/37, 102, 103

[56] References Cited

U.S. PATENT DOCUMENTS

| | | | |
|---|---|---|---|
| 3,104,209 | 9/1963 | Scott | 422/56 X |
| 3,654,179 | 4/1972 | Bauer | 422/56 X |
| 3,713,986 | 1/1973 | Bergmeyer et al. | 23/230 B |
| 3,988,208 | 10/1976 | Werner et al. | 435/28 X |
| 4,141,688 | 2/1979 | Morris et al. | 23/230 B |
| 4,295,853 | 10/1981 | Kasahara et al. | 436/66 |
| 4,384,042 | 5/1983 | Miike et al. | 435/28 X |

FOREIGN PATENT DOCUMENTS

| | | |
|---|---|---|
| 70887 | 6/1979 | Japan . |
| 92391 | 7/1979 | Japan . |
| 23401 | 2/1980 | Japan . |
| 43481 | 3/1980 | Japan . |

Primary Examiner—Robert J. Hill, Jr.
Attorney, Agent, or Firm—Fitzpatrick, Cella, Harper & Scinto

[57] ABSTRACT

A method for the determination of peroxide in a sample is disclosed which comprises reacting the peroxide with a chromogen represented by the general formula (I) or (II)

general formula (I):

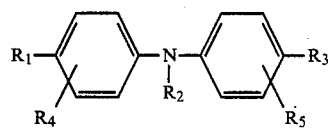

general formula (II):

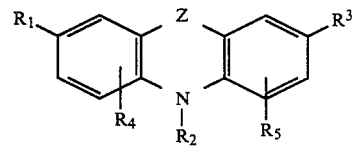

wherein $R_1$ and $R_3$ represent amino, mono- or di- substituted amino, hydroxyl or hydroxyalkyl, $R_4$ and $R_5$ represent hydrogen, alkyl, alkylene, acyl, halogen, sulphone, nitro, carboxyl, hydroxyl or hydroxyalkyl, $R_2$ represents hydrogen,

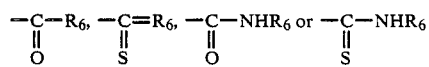

wherein $R_6$ represents hydrogen, alkyl, aralkyl, alkylene, aryl or mono- or di- substituted aryl, and —Z— may change to =Z= by resonance and represents —S—, —O—, —N=,

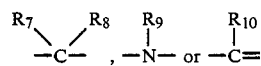

wherein $R_7$, $R_8$, $R_9$ and $R_{10}$ have the same significance as $R_6$ in the presence of heme compound, iodide or bromide and measuring the absorbancy of the reaction solution in the visible ray region. Also disclosed is a test composition for the determination of peroxide which comprises a chromogen as defined above and a compound selected from a heme compound, iodide and bromide.

7 Claims, No Drawings

METHOD AND TEST COMPOSITION FOR DETERMINATION OF LIPID PEROXIDE

This application is a continuation of application Ser. No. 858,088 filed Apr. 29, 1986, (now abandoned) which is a continuation of appln. Ser. No. 758,566, filed July 24, 1985 (now abandoned), which is a continuation of appln. Ser. No. 552,006, filed Nov. 14, 1983 (now abandoned), which is a continuation of appln. Ser. No. 445,431, filed Nov. 30, 1982 (now abandoned), which is a continuation of appln. Ser. No. 253,546, filed Apr. 13, 1981 (now abandoned).

The present invention relates to a method for the determination of peroxide. More particularly, it relates to a method for the determination of peroxide in a sample by reacting the peroxide with a compound which is converted to a pigment by oxidation (hereinafter referred to as "chromogen") in the presence of a heme compound, iodide or bromide and measuring the absorbancy of the reaction solution colored in the visible ray region.

The determination of peroxide in vivo is recognized as important for the diagnosis of arteriosclerosis, diabetes mellitus, etc.

As the methods for the determination of peroxide in a sample, direct methods such as iodide titration method, rohdan iron method, chromatograph method and ultraviolet absorption method and indirect method such as thiobarbituric acid method are known. However, these methods are not satisfactory with respect to sensitivity, and further they require the removal of the substance contained in the sample and affecting the determination.

Recently, a method has been proposed wherein peroxide is determined by reacting peroxide with a chromogen in the presence of a kind of metal compound and by measuring the absorbancy of the reaction solution colored by the formation of pigment. (Japanese Published Unexamined Patent Application Nos. 92391/79 and 23401/80). A simple method which is excellent in sensitivity is in demand.

To this end, studies have been made, and it has been found that peroxide and cumene hydroperoxide are determined by reaction with a chromogen represented by the general formula (I) or (II) below to form a pigment, followed by measurement of the absorbancy of the colored reaction solution in the visible ray region.

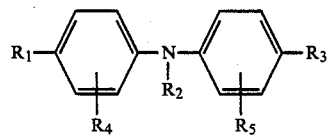

Formula (I)

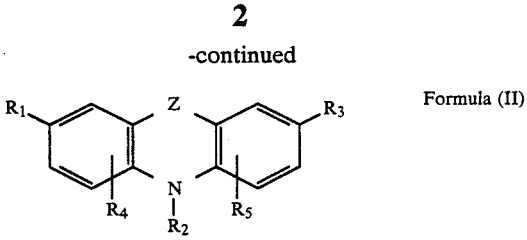

Formula (II)

In the formulae, $R_1$ and $R_3$ represent amino, mono- or di-substituted amino, hydroxyl or hydroxyalkyl, $R_4$ and $R_5$ represent hydrogen, alkyl, alkylene, acyl, halogen, sulphone, nitro, carboxyl, hydroxyl or hydroxyalkyl, $R_2$ represents hydrogen,

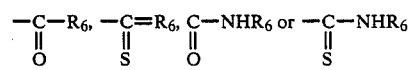

wherein $R_6$ represents hydrogen, alkyl, aralkyl, alkylene, aryl or mono- or di-substituted aryl, and —Z— may change to —Z= by resonance and represents —S—, —O—, —N=,

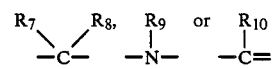

wherein $R_7$, $R_8$, $R_9$ and $R_{10}$ have the same significance as $R_6$. When Z has three bonds, the position of the double bond of the compound represented by the general formula (II) may change.

Substituents of substituted amino in $R_1$ and $R_3$ include alkyl, alkylene, hydroxyalkyl, acylaminoalkyl and acyl. As the substituted aryl in $R_6$, substituted phenyl is exemplified and the substituents include halogen, alkyl, amino, acylamino, and alkoxycarbonylamino. Aryl includes phenyl.

As an aralkyl, phenylaklyl such as benzyl and substituted phenylakyl such as substituted benzyl are exemplified. The substituents have the same significance as those in the substituted aryl mentioned above.

In the above definition, alkyl includes an alkyl group having 1-6 carbon atoms and methyl, ethyl, propyl, butyl, pentyl, hexyl and cyclohexyl are exemplified. Acyl includes an acyl group having 2-5 carbon atoms, and acetyl and propionyl are exemplified. Alkoxy include an alkoxy group having 1-5 carbon atoms and methoxy, ethoxy, propoxy and butoxy are exemplified.

These compounds are generally known and are easily prepared by the methods illustrated by the following reaction formulae.

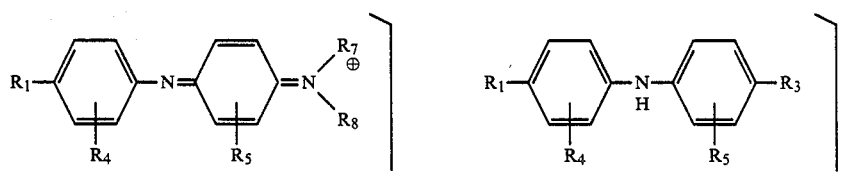

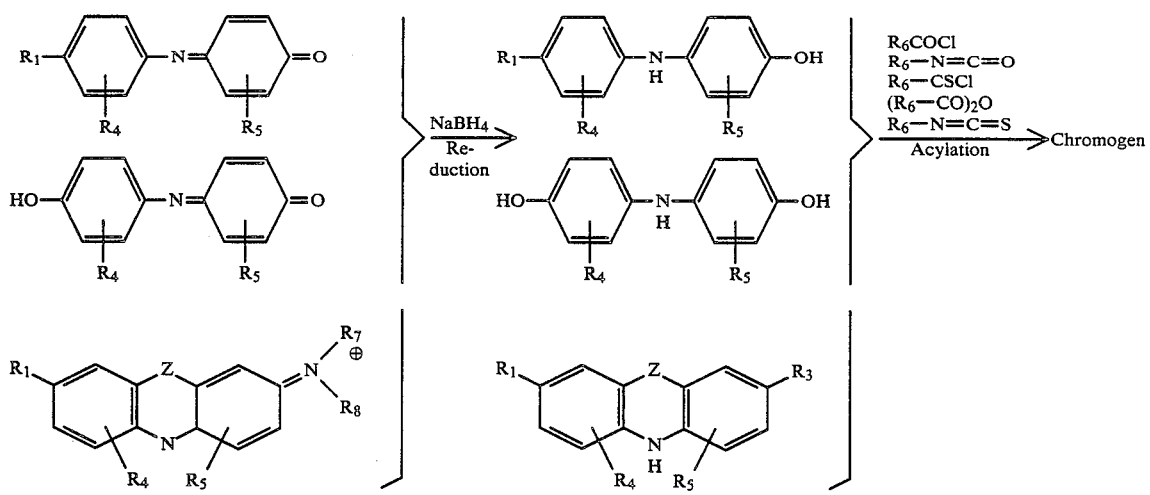

The principal of the present invention is on the basis of the fact that the reaction of peroxide or cumene hydroperoxide with a chromogen in the presence of heme compound, iodide or bromide proceeds stoichiometrically to form a pigment and the amount of formed pigment is proportioal to the amount of peroxide or cumene hydroperoxide in the sample.

The principle is illustrated as follows.

[General formula (I')]

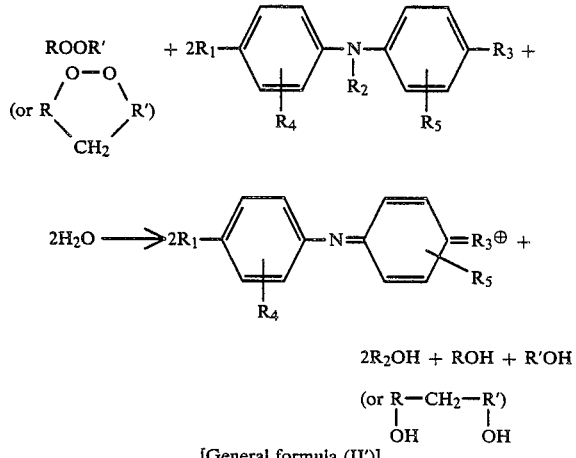

[General formula (II')]

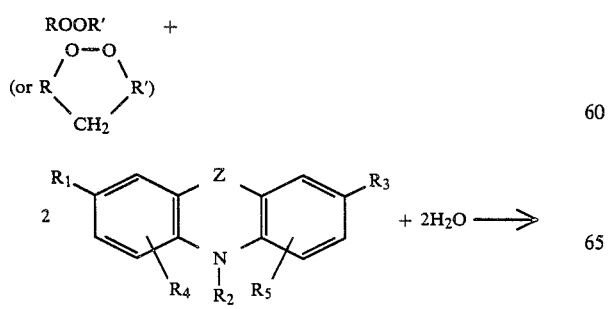

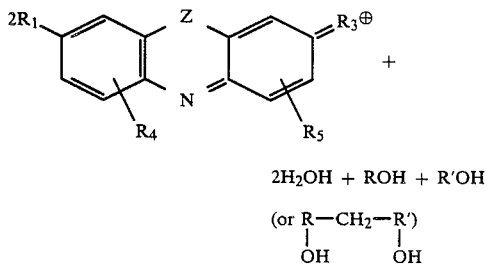

[General formula (I')]

$$ROOR' + 2KX + 2H_2O \longrightarrow ROH + R'OH + 2KOH + X_2$$

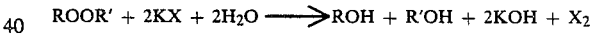

[General formula (II')]

In the above formulae, $R_1$, $R_2$, $R_3$, $R_4$, $R_5$ and Z have the same significance as defined above and X is I or Br. ROOR' and

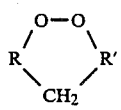

represent a peroxide.

As is apparent form the above equations, one molecule of the compound represented by the general formula (I') or (II') per one —O—O— group is produced by the reaction and therefore the number of the —O—O— groups in a sample is determined according to the present invention.

The compounds represented by the general formula (I') or (II') are generally known pigments which exhibit a characteristic absorption at the wavelength between 500-800 nm and have a large value of molecular extinction coefficient.

According to the present invention, the present method is applied to the determination of peroxide in a sample such as serum, blood, etc.

In carrying out the present method, a sample is used as itself or after dilution with water, propanol, etc. and if necessary the solution is subjected to centrifugation to remove the substance which may interfere with the measurement and the supernatant is used as a test sample. Usually the sample is used in a concentration of 1-500 nmol/ml, preferably 30-200 nmol/ml as —O—O— group.

The sample is added to the appropriate buffer solution, preferably, buffer having a pH of 2-10. Then to the solution are added, (1) heme compound, iodide or bromide (2) chromogen represented by the general formula (I) or (II) and if necessary, (3) surfactant for promoting the dissolution of peroxide, a chelating reagent such as EDTA for chelating the metal in the sample and sodium chloride for inhibiting the ceruloplasmin activity.

The reaction is carried out at a temperature of 10°-15° C., preferably 30°-40° C. and usually completes in 5-30 minutes. After completio of the reaction, the absorbancy of the reaction solution ($E_S$) is measured at the characteristic absorption wavelength of the pigment formed from chromogen.

The diluent used for the dilution of sample and the standard compound such as cumene hydroperoxide are subjected to the same procedures as described above to obtain blank absorbancy ($E_B$) and standard absorbancy ($E_{STD}$).

The concentration of peroxide ($L_p$) is calculated by the following equation.

$$L_p = \frac{E_S - E_B}{E_{STD} - E_B} \times A$$

A: the concentration of peroxide in standard solution

As the heme compound used in the present invention, hemoglobin, myoglobin and iron chlorophyllin are exemplified.

Iodide and bromide include alkaline metal salts such as potassium salt, sodium salt and lithium salt and alkali earth metal salts such as calcium salt, aluminum salt and balium salt of iodide or bromine. The heme compound is used in a concentration of 0.1 mg/120 g/l. Iodide and bromide are usually used in a concentration of 1-100 mg/ml. Surfactant, chelating agent and sodium chloride are used in a concentration of 0.001-10%. Chromogen is used in a concentration of 0.001-1 mg/ml.

As buffers, phosphate buffer, tris-HCl buffer, succinate buffer, citrate buffer, acetate buffer, etc. may be used in a concentration of 0.005-2 mol/l.

Examples of the chromogen used in the present invention are shown in Table 1. The symbols in Table 1 have the following meaning.

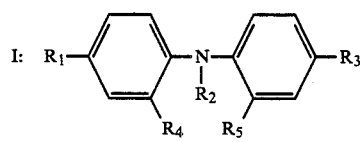

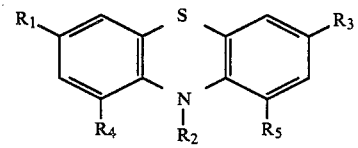

A: $N(CH_3)_2$

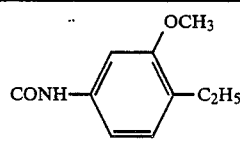

G:

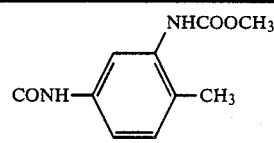

Q:

B: $N(C_2H_5)_2$

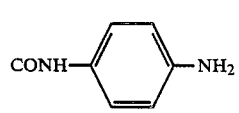

K:

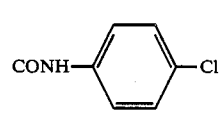

$Y_p$:

D: 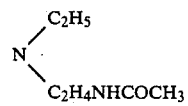

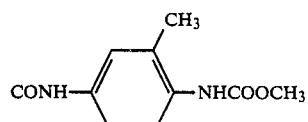

L:

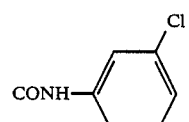

$Y_m$:

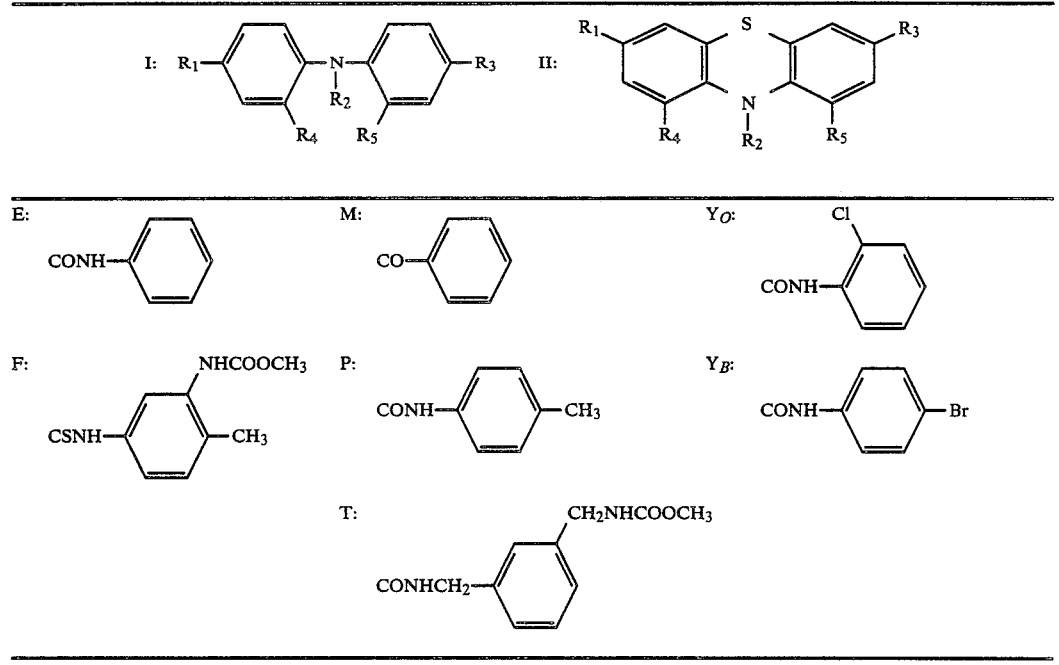

TABLE 1

| Compound number | Formula | R₁ | R₂ | R₃ | R₄ | R₅ |
|---|---|---|---|---|---|---|
| 1 | I | A | H | A | H | H |
| 2 | I | NH₂ | H | A | H | H |
| 3 | I | A | H | A | CH₃ | CH₃ |
| 4 | I | A | E | B | H | H |
| 5 | I | D | F | D | H | H |
| 6 | I | D | H | D | CH₃ | CH₃ |
| 7 | I | A | G | OH | CH₃ | H |
| 8 | I | OH | K | OH | CH₃ | H |
| 9 | I | A | L | B | H | OH |
| 10 | II | A | H | A | H | H |
| 11 | II | A | M | A | H | H |
| 12 | II | B | P | D | CH₃ | H |
| 13 | II | D | Q | D | H | H |
| 14 | II | D | Q | OH | CH₃ | CH₃ |
| 15 | II | A | $Y_P$ | A | H | H |
| 16 | II | A | $Y_O$ | A | H | H |
| 17 | II | A | $Y_m$ | A | H | H |
| 18 | II | A | $Y_B$ | A | H | H |
| 19 | II | A | E | A | H | H |
| 20 | II | A | T | A | H | H |

The degree of color development, the stability of color and the influence of the components in serum on the determination value when Compound (I) is used as a chromgen, are illustrated by the following experiment.

Experiment 1

Compound Nos. 1-20 in the amount indicated in Table 2 are dissolved in 1 ml of dimethylformamide (hereinafter referred to as "DMF"). The test reagent is prepared by adding 0.1 g Triton X-100, DMF solution of Compound Nos. 1-20, 1 g of EDTA and 6.7 mg of hemoglobin to 100 ml of 0.1 M phosphate buffer (pH 5.0).

3 ml of the reagent solution is poured into a test tube for each compound and linolic acid (A) is added thereto. The reaction is carried out at 37° C. for 30 minutes and the absorbancy of the reaction solution ($E_S$) is measured. The blank absorbancy ($E_B$) is measured by repeating the above procedures without the addition of linolic acid.

As a control, the absorbancies ($E_{SC}$ and $E_{BC}$) are measured using 4-amino antipyrine (hereinafter referred to as 4 AA) and m-methyl-(N-ethyl, N-acetoaminoethyl) aniline (hereinafter referred to as EMAE) as coloring reagent, and the degree of color development of test compound is calculated from the following equation defining the degree of color development of control as 100.

$$\text{Degree of color development} = \frac{E_S - E_B}{E_{SC} - E_{BC}} \times 100$$

The stability of color is determined as follows. The reaction solution is further incubated at 37° C. for 30 minutes and $E_S - E_B$ is calculated. "S₀" means that the value of $E_S - E_B$ was not changed by this incubation and "S₁" means that the change of the value is 10% or less. The influence of bilirubin and vitamin C in the sample on the determination value is indicated by the value M. The value M is determined by repeating the above experiment using the sample containing 4 μg/3 ml of bilirubin or 2 μg/3 ml of vitamin C, measuring the absorbancy ($E_{S'}$) and calculating from the following equation:

$$M = \frac{E_S - E_{S'}}{E_S - E_B} \times 100 \, (\%)$$

The symbol (—) means that the value (M) is 3% or less. The symbol (±) means that the value is 3-6% and (+) for 6-20% and (++) for 20% or more.

TABLE 2

| | Chromogen | Degree of color | Inhibitor | | |
|---|---|---|---|---|---|
| No. | Amount mg | development | $B_i$ | $V_c$ | Stability |
| 1 | 10.0 | 538 | — | — | S₀ |

TABLE 2-continued

| Chromogen | | Degree of color development | Inhibitor | | Stability |
|---|---|---|---|---|---|
| No. | Amount mg | | $B_i$ | $V_c$ | |
| 2 | 10.0 | 313 | − | − | $S_1$ |
| 3 | 12.0 | 277 | − | ± | $S_0$ |
| 4 | 14.7 | 495 | − | ± | $S_0$ |
| 5 | 23.4 | 532 | − | ± | $S_0$ |
| 6 | 16.8 | 575 | − | − | $S_0$ |
| 7 | 16.4 | 251 | + | ± | $S_1$ |
| 8 | 14.3 | 304 | + | + | $S_1$ |
| 9 | 19.2 | 527 | − | ± | $S_0$ |
| 10 | 11.2 | 572 | − | ± | $S_0$ |
| 11 | 15.0 | 470 | − | ± | $S_0$ |
| 12 | 21.4 | 581 | − | ± | $S_0$ |
| 13 | 24.8 | 519 | − | ± | $S_0$ |
| 14 | 22.1 | 294 | ± | + | $S_0$ |
| 15 | 3.1 | 506 | − | ± | $S_0$ |
| 16 | 3.1 | 311 | ± | ± | $S_0$ |
| 17 | 3.1 | 547 | − | ± | $S_0$ |
| 18 | 10.0 | 523 | − | ± | $S_0$ |
| 19 | 3.3 | 536 | − | ± | $S_0$ |
| 20 | 3.3 | 478 | − | ± | $S_0$ |
| Control | 4 AA:6.7 EMAE:26.6 | 100 | − | ± | $S_0$ |
| Comparison 1 | 4 AA:6.7 Phenol:33 | 43.4 | ++ | + | $S_0$ |
| Comparison 2 | M-T method | 210 | ++ | + | $S_0$ |

$B_i$: bilirubin
$V_c$: vitamin C
M-T: malon dialdehyde-thiobarbituric acid

For comparison, 4 AA-phenol or malon dialdehyde-thiobarbituric acid is used as a chromogen and the results are shown in Table 2.

Another aspect of the present invention is to provide a test composition for the determination of peroxide which comprises a chromogen represented by the general formula (I) or (II), a compound selected from heme compound, iodide and bromide and a buffer. The composition may contain a surfactant, chelating reagent and sodium chloride.

The composition may be used in various forms. For example, the ingredients may be mixed in liquid form or powder form.

Certain specific embodiments of the present invention are illustrated by the following representative examples.

EXAMPLE 1

The test reagent is prepared by adding 0.1 g of Tricon X-100, 1 ml of DMF solution containing 10 mg of Compound 1, 5.6 mg of hemoglobin and 1 g of EDTA to 100 ml of 0.1 M phosphate buffer (pH 5.0).

As the sample containing peroxide, 1 ml of linolic acid (A) and 1 ml of linolenic acid (B) are respectively diluted with isopropanol to make 100 ml of a solution.

20 μl of the test sample is added to 3 ml of the test reagent and incubated at 37° C. with stirring. The absorbancy of the reaction solution at 728 nm is monitored for 10 minutes from the start of the reaction. The absorbancy reaches equilibrium within about 5 minutes.

The same procedures as described above are repeated except that cumene hydroperoxide is used as a standard compound and the absorbancy of the reaction solution at 728 nm is measured about 10 minutes from the start of the reaction. The standard curve between the absorbancy and the concentration of peroxide is prepared by repeating the above procedure varying the concentration of cumene hydroperoxide.

The peroxide values for the samples containing linolic acid (A) and linolenic acid (B) are calculated from the standard curve to obtain 37 for (A) and 29.5 for (B).

For comparison, peroxide values of the samples are determined according to the known iodide titration method to obtain 35.1 for (A) and 21.3 for (B).

The present method and the known method described above are repeated five times for samples (A) and (B). The coefficient of variation by the present method is 0.1% for (A) and 0.15% for (B) and that by the known method is 10.5% for (A) and 12.3% for (B).

EXAMPLE 2

The samples indicated in Table 3 are dissolved in water or isopropanol in a ratio of 10% (V/V). 50 μl of each solution is added to 3 ml of the test reagent of Example 1. The reaction is carried out under the same conditions as in Example 1 and the absorbancy of the reaction solution is measured.

The results are shown in Table 3.

TABLE 3

| Sample | Solvent | The amount of peroxide*1 (nmol/g) | C.V (%)[2] |
|---|---|---|---|
| 1 | Distilled water | 390.7 | 0.31 |
| 2 | " | 274.4 | 0.52 |
| 3 | " | 135.9 | 0.86 |
| 4 | " | 183.1 | 0.42 |
| 5 | Isopropanol | 15.2 | 3.21 |

1: Emulgen 404 (non-ionic surfactant, product of Kao Atras Co., Ltd.)
2: Emul 20T (anionic surfactant, product of Kao Atras Co., Ltd.)
3: Quartamin 86P (cationic surfactant, product of Kao Atras Co., Ltd.)
4: Tetrahydrofuran
5: Ethylether
*1: The value is the average of five measurements.
*2: CV: coefficient of variation

EXAMPLE 3

In this example, 0.2 ml of normal and patient serum are added to 4 ml of isopropanol and the solutions are subjected to centrifugation at 2,000 r.p.m. for 5 minutes. To 0.5 ml of the supernatant is added 3 ml of the test reagent of Exampole 1, and the mixture is incubated at 37° C. for 10 minutes. The absorbancy of the reaction solution ($E_S$) is measured at 728 nm.

The same procedures as described above are repeated for 0.5 ml of 200 nmol/ml cumene hydroperoxide isopropanol solution and 0.5 ml of isopropanol to obtain the absorbancies $E_{STD}$ and $E_B$. The amount of peroxide ($L_P$) in serum calculated from the following equation is 15.2 nmol/ml for normal and 96.3 nmol/ml for patient.

$$L_p(\text{nmol/ml}) = \frac{E_S - E_B}{E_{STD} - E_B} \times 200$$

EXAMPLE 4

The same procedures as described in Example 1 are repeated except that the compounds indicated in Table 4 instead of Compound 1 are used as chromogen and the peroxide values (PA) for sample (A) and (PB) for sample (B) are determined. The results are shown in Table 4.

TABLE 4

| Chromogen | Wavelength (nm) | Reaction time (min.) | PA (nmol/Kg) | PB (nmol/Kg) |
| --- | --- | --- | --- | --- |
| 2 | 700 | <5 | 38.5 | 30.4 |
| 3 | 720 | <5 | 38.3 | 29.9 |
| 4 | 720 | 15 | 36.9 | 25.1 |
| 5 | 730 | 15 | 37.2 | 26.2 |
| 6 | 730 | <5 | 38.9 | 28.9 |
| 7 | 600 | 20 | 40.3 | 30.5 |
| 8 | 600 | 20 | 36.1 | 26.4 |
| 9 | 720 | 15 | 39.2 | 29.8 |
| 10 | 665 | <5 | 38.5 | 28.7 |
| 11 | 665 | 20 | 37.1 | 26.8 |
| 12 | 670 | 15 | 37.2 | 27.0 |
| 13 | 670 | 16 | 36.8 | 26.1 |
| 14 | 620 | 20 | 35.9 | 26.5 |
| 19 | 665 | <5 | 39.0 | 27.3 |

EXAMPLE 5

The same procedures as described in Example 1 are repeated except that 0.56 mg of sodium salt or iron chlorophyllin or 5.6 mg of myoglobin (Sigma Co.) is used instead of hemoglobin. The peroxide value obtained using iron chlorophyllin is 38.2 for sample (A) and 29.3 for sample (B) and that obtained using myoglobin is 37.8 for sample (A) and 28.5 for sample (B).

EXAMPLE 6

In this example, 0.1 g of Triton X-100, 1 ml of DMF solution containing 10 mg of Compound 1, 1 g of potassium iodide and 1 g of EDTA are dissolved in 100 ml of 0.1 M phosphate buffer (pH 4.0) and the solution is used as test reagent.

The same procedures as described in Example 1 are repeated using the test reagent for 50 μl of sample (A) or (B). The peroxide value is 37.5 for sample (A) and 28.7 for sample (B).

EXAMPLE 7

In this example, as the standard peroxide, linolic acid is oxidized with air at 23° C. for 72 hours according to the method described in Canad. J. Biochem. 47, 485 (1969). The oxidation product is subjected to extraction with a solvent system of petroleum ether/67% methanol—33% water. The layer of methanol—water is concentrated to obtain an oily matter. The oily matter is subjected to thin layer chromatography using silica gel and hexane—ether—acetic acid (60:40:1) as a developer. Silica gel showing an Rf value of 0.23 is subjected to elution using ethanol and the eluate is concentrated to obtain a racemic mixture of equimolar amounts of linolic acid having —OOH at the 9-position and linolic acid having —OOH at the 13-position. 310.4 mg of the obtained mixture is dissolved in 1 l of isopropanol to obtain 1 μmol/ml solution (hereinafter referred to as test solution).

The test reagent is prepared by adding 0.1 g of Triton X-100, 1 ml of DMF solution containing 10 mg of Compound 20, 5.6 mg of hemoglobin and 1 g of EDTA to 100 ml of 0.1 M phosphate buffer (pH 5.0).

The test solution is diluted ten-fold with isopropanol. 100 μl of the diluted test solution is added to 3 ml of the test reagent in a test tube and 100 μl of isopropanol is added to 3 ml of the test reagent in another test tube. The mixtures are incubated at 37° C. for ten minutes and the absorbancies of the reaction solutions are measured at 666 nm to obtain O.D. values of 0.308 and 0.085 respectively. The increase in absorbancy by the addition of oxidized linolic acid is calculated as 0.223.

Then, 391.9 mg of Methylene Blue is dissolved in 1 l of water and the solution is diluted ten-fold with water. 100 μl of the blue colored solution is added to 0.1 M phosphate buffer (pH 5.0) and the absorbancy of the solution is measured to obtain a value of 0.225.

Then, 100 μl of the test solution having the concentration indicated in Table 5 is added to 3 ml of the test reagent and the mixture is incubated at 37° C. for ten minutes. The absorbancy ($E_N$) of the reaction solution is measured at 666 nm. As a blank, the same procedures as described above are repeated except using isopropanol instead of the test solution and the absorbancy ($E_B$) is measured at 666 nm. The results are shown in Table 5. As is apparent from the table, the concentration of oxidized linolic acid is proportional to the value of $E_N - E_B$.

TABLE 5

| Concentration of linolic acid (nmol/ml) | 0 | 25 | 50 | 100 | 150 |
| --- | --- | --- | --- | --- | --- |
| $E_N - E_B$ | 0 | 0.057 | 0.113 | 0.227 | 0.340 |

EXAMPLE 8

In this example, 100 μl of isopropanol solution of cumene hydroperoxide having the concentration indicated in Table 6 is added to 3 ml of 50 mM citrate buffer (pH 4.7) containing 1 mg/ml Emulgen 106 (non-ionic surfactant, product of Kao Atras Co., Ltd.), 5 mg/dl hemoglobin and 2.5 mg/dl Compound 18.

The mixture is incubated at 37° C. for 30 minutes. The absorbancy of the reaction solution ($E_N$) is measured at 666 nm.

As a blank test, the same procedures as described above are repeated except using isopropanol instead of cumene hydroperoxide solution and the absorbancy ($E_B$) is measured.

The results are shown in Table 6. As is apparent from the table, the concentration of cumene hydroperoxide is proportional to the value of $E_N - E_B$.

TABLE 6

| Concentration of cumene hydroperoxide (nmol/ml) | 0 | 25 | 50 | 100 | 150 |
| --- | --- | --- | --- | --- | --- |
| $E_N - E_B$ | 0 | 0.056 | 0.113 | 0.225 | 0.336 |

REFERENCE EXAMPLE 1

In this example, 1 g of Methylene Blue is dissolved in 100 ml of water and 1 g of sodium borohydride is added little by little to proceed the reduction. When the precipitate of leuco base is desposited and the solution is discolored, 20 ml of chloroform is added and the mixture is vigorously stirred to extract leuco base.

The chloroform layer is filtered through filter paper, dehydrated and desalted. Then, 2 ml of phenyl isocyanate is added and the mixture is subjected to reaction at room temperature for 24 hours.

After completion of the reaction, methanol is added to remove excess isocyanate and the mixture is stirred at room temperature for 3 hours.

The mixture is subjected to column chromatography using silica gel having the size of 60-80 mesh (product of Kanto Kagaku Co., Ltd.) and using chloroform as a developer to obtain Compound 19 having a melting point of 100°-115° C.

REFERENCE EXAMPLE 2

The same procedures as described in Reference Example 1 are repeated except that o-, m- or p-chlorophenyl uisocyanate or p-bromophenyl isocyanate is used instead of phenylisocyanate to obtain Compound 16 (oil form), Compound 17 (m.p. 73°-77° C.), Compound 15 (m.p. 76°-83° C.) and Compound 18 (m.p. 80°-90° C.), respectively.

What is claimed is:

1. A method for determining lipid peroxide in a sample which comprises:

contacting a sample with a chromogen represented by the general formula (I) or (II)

general formula (I):

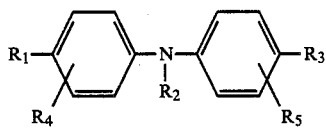

general formula (II):

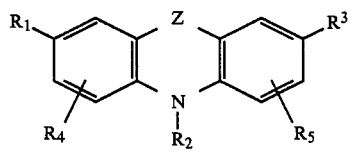

wherein $R_1$ and $R_3$ represent amino, mono- or di-substituted amino, hydroxyl or hydroxyalkyl; $R_4$ and $R_5$ represent hydrogen, alkyl, alkylene, acyl, halogen, sulphone, nitro, carboxyl, hydroxyl or hydroxyalkyl; $R_2$ represents

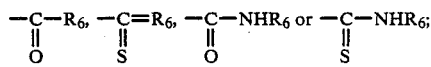

wherein $R_6$ represents hydrogen, alkyl, aralkyl, alkylene, aryl or mono or di-substituted aryl; and —Z— may change to —Z= by resonance and represents —S—, —O—, —N=,

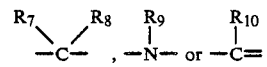

wherein $R_7$, $R_8$, $R_9$ and $R_{10}$ have the same significance as $R_6$ in the presence of a heme compound, iodide to bromide to form a reaction solution; and measuring the absorbancy of the reaction solution in the visible ray region.

2. The method according to claim 1, wherein the sample is contacted with the chromgen in the presence of a heme compound selected from the group consisting of hemoglobin, myoglobin and iron chlorophyllin to form the reaction solution.

3. The method according to claim 1, wherein said reaction solution includes a buffer solution.

4. A test composition for determining peroxide which comprises a chromogen as defined in claim 1 and a compound selected from the group consisting of a home compound, iodide and bromide.

5. The composition according to claim 4, wherein the composition comprises the chromogen and a heme compound selected from the group consisting of hemoglobin, myoglobin and iron chlorophyllin.

6. The composition according to claim 4, which additionally comprises a buffer.

7. The composition according to claim 6, which additionally comprises at least one member selected from the group consisting of a surfactant, a chelating reagent or sodium chloride.

* * * * *

UNITED STATES PATENT AND TRADEMARK OFFICE
CERTIFICATE OF CORRECTION

PATENT NO. : 4,851,353
DATED : July 25, 1989
INVENTOR(S) : AKIRA MIIKE, ET AL.

It is certified that error appears in the above-identified patent and that said Letters Patent is hereby corrected as shown below: Title page:

IN [63] RELATED U.S. APPLICATION DATA

"Ser. No. 522,006, Nov. 14, 1983," should read
--Ser. No. 552,006, Nov. 14, 1983--.

COLUMN 3

Line 31, "proportioal" should read --proportional--.

COLUMN 5

Line 11, "form" should read --from--.

COLUMN 6

Line 5, "completio" should read --completion--.
Line 27, "balium salt" should read --barium salt-- and "iodide" should read --iodine--.

COLUMN 7

Line 53, "chromgen," should read --chromogen,--.

COLUMN 9

TABLE 2-continued, for Chromogen No. 4, in the column for $V_c$, "±" should read --+--.
Line 48, "Tricon" should read --Triton--.

COLUMN 10

Line 18, "reactionis" should read --reaction is--.
Line 45, "Exampole 1," should read --Example 1,--.

UNITED STATES PATENT AND TRADEMARK OFFICE
CERTIFICATE OF CORRECTION

PATENT NO. : 4,851,353
DATED : July 25, 1989
INVENTOR(S) : AKIRA MIIKE, ET AL.

It is certified that error appears in the above-identified patent and that said Letters Patent is hereby corrected as shown below:

COLUMN 11

Line 57, "obtaina" should read --obtain a--.

COLUMN 13

Line 13, "uisocyanate" should read --isocyanate--.(2nd occurr)

COLUMN 14

Line 9, "mono or" should read --mono- or--.
　　　Line 18, "to bromide" should read --or bromide--.
　　　Line 22, "chromgen" should read --chromogen--.
　　　Line 30, "home" should read --heme--.

Signed and Sealed this

Seventh Day of August, 1990

Attest:

HARRY F. MANBECK, JR.

*Attesting Officer*　　　*Commissioner of Patents and Trademarks*